US011378578B2

(12) United States Patent
Wu et al.

(10) Patent No.: US 11,378,578 B2
(45) Date of Patent: Jul. 5, 2022

(54) REAGENTS, SYSTEMS AND METHODS FOR ANALYZING ERYTHROCYTES AND PLATELETS

(71) Applicant: Abbott Laboratories, Abbott Park, IL (US)

(72) Inventors: Jiong Wu, Los Gatos, CA (US); Ji Lin, San Jose, CA (US)

(73) Assignee: Abbott Laboratories, Abbott Park, IL (US)

( * ) Notice: Subject to any disclaimer, the term of this patent is extended or adjusted under 35 U.S.C. 154(b) by 910 days.

(21) Appl. No.: 14/137,392

(22) Filed: Dec. 20, 2013

(65) Prior Publication Data
US 2014/0273061 A1   Sep. 18, 2014

Related U.S. Application Data

(60) Provisional application No. 61/778,051, filed on Mar. 12, 2013.

(51) Int. Cl.
| | |
|---|---|
| *G01N 15/14* | (2006.01) |
| *G01N 21/47* | (2006.01) |
| *G01N 33/49* | (2006.01) |
| *G01N 15/10* | (2006.01) |
| *G01N 15/00* | (2006.01) |
| *G01N 15/02* | (2006.01) |
| *G01N 33/569* | (2006.01) |

(52) U.S. Cl.
CPC ... *G01N 33/56972* (2013.01); *G01N 15/1434* (2013.01); *G01N 15/1459* (2013.01); *G01N 21/47* (2013.01); *G01N 33/49* (2013.01); G01N 15/0205 (2013.01); G01N 2015/0073 (2013.01); G01N 2015/0076 (2013.01); G01N 2015/0084 (2013.01); G01N 2015/0277 (2013.01); G01N 2015/1006 (2013.01); G01N 2015/1477 (2013.01); G01N 2015/1493 (2013.01)

(58) Field of Classification Search
None
See application file for complete search history.

(56) References Cited

U.S. PATENT DOCUMENTS

| | | | | |
|---|---|---|---|---|
| 5,227,304 A | * | 7/1993 | Wong | G01N 33/5094 436/17 |
| 5,631,165 A | * | 5/1997 | Chupp | B01F 5/0453 422/63 |
| 5,656,499 A | | 8/1997 | Chupp et al. | |
| 5,812,419 A | * | 9/1998 | Chupp | G01N 35/1004 702/20 |
| 6,225,124 B1 | * | 5/2001 | Houwen | G01N 33/5094 252/408.1 |
| 6,228,652 B1 | * | 5/2001 | Rodriguez | G01N 15/14 356/335 |
| 7,824,916 B2 | * | 11/2010 | Fujimoto | G01N 15/1404 252/408.1 |
| 7,968,279 B2 | | 6/2011 | Van Agthoven et al. | |
| 2003/0025896 A1 | * | 2/2003 | Oever | G01N 15/1456 356/39 |
| 2003/0180955 A1 | * | 9/2003 | Ozasa | G01N 15/1404 436/10 |
| 2004/0018629 A1 | | 1/2004 | Kawate | |
| 2009/0220936 A1 | | 9/2009 | Van Agthoven et al. | |
| 2010/0081161 A1 | * | 4/2010 | Mori | G01N 1/38 435/29 |
| 2010/0105074 A1 | * | 4/2010 | Covey | G01N 35/00722 435/7.1 |
| 2010/0247383 A1 | * | 9/2010 | Okubo | G01N 35/00693 422/82.02 |
| 2011/0178716 A1 | * | 7/2011 | Krockenberger | G01N 15/147 702/19 |
| 2012/0282600 A1 | | 11/2012 | Wu et al. | |

FOREIGN PATENT DOCUMENTS

| | | |
|---|---|---|
| CN | 1265196 A | 8/2000 |
| CN | 101685050 A | 3/2010 |
| CN | 101975850 A | 2/2011 |
| JP | 10-160730 H | 6/1998 |
| JP | 2002-540426 T | 11/2002 |
| WO | 0058727 | 10/2000 |
| WO | 2003021223 A2 | 3/2003 |

OTHER PUBLICATIONS

MCV, MCV definition, Medscape Reference webpage, 2016.*
MCV, Curry et al., Mean Corpuscular Volume (MCV), Medscape reference., Jan. 13, 2015.*
Yue, Jiaxin, et al., "Detection of Principles of Blood Cell Analyzers", Chinese Journal of Laboratory Medicine 27(3), 2004, 205-208.

* cited by examiner

*Primary Examiner* — Louise W Humphrey
*Assistant Examiner* — Srikanth Patury
(74) *Attorney, Agent, or Firm* — Bozicevic, Field & Francis LLP; Edward J. Baba; Mandar A. Joshi

(57) ABSTRACT

Aspects of the invention include hematology analysis reagents, systems and methods that can be used to preserve blood cell morphology and integrity as well as provide sample integrity and optical clarity to facilitate optical analysis of blood samples. In some embodiments, the reagents include a non-phosphate organic buffer and a sphering surfactant. The pH and osmolality of the reagents may be adjusted to desired ranges. In addition, the reagents can be simply diluted with de-ionized water prior to use.

22 Claims, 4 Drawing Sheets

REAGENTS, SYSTEMS AND METHODS FOR ANALYZING ERYTHROCYTES AND PLATELETS

CROSS-REFERENCE

This application claims the benefit of U.S. Provisional Patent Application No. 61/778,051 filed Mar. 12, 2013, which application is incorporated herein by reference in its entirety.

INTRODUCTION

Diluent reagents have broad applications in hematology analyses, serving as, e.g., diluting reagents in the preparation of blood samples for analysis of red blood cells (RBCs), platelets (PLTs), and/or reticulocytes (RETCs). Diluent solutions also serve as, e.g., sheath solutions, rinsing solutions, maintenance solutions that prevent drying or salt precipitation on instrumentation, and the like. As such, diluent reagents for use with hematology analyzers are by far one of the largest consumable reagents in the hematology field.

In current configurations, due to consumption rates, diluent solutions are typically stored in large containers that are heavy and difficult to manipulate. In some cases, for example, 20 liter cubitainers are used to store diluent reagents. Such containers are large and heavy, and present ergonomic issues for those who work with them. In addition, these heavy containers are expensive to ship and take up large amounts of storage space. Accordingly, there is clearly a need for more concentrated diluent reagents that would eliminate, or at least reduce the magnitude of these issues. The present invention addresses these and other needs.

SUMMARY

Aspects of the invention include hematology analysis reagents, systems and methods that can be used to preserve blood cell morphology and integrity as well as provide sample integrity and optical clarity to facilitate optical analysis of blood samples. In some embodiments, the reagents include a non-phosphate organic buffer and a sphering surfactant. The pH and osmolality of the reagents may be adjusted to desired ranges. In addition, the reagents can be simply diluted with de-ionized water prior to use.

In some embodiments, the present disclosure provides systems for conducting an optical mean corpuscular volume (MCV) analysis on a sample of whole blood, the system comprising: (a) a hematology analyzer, the hematology analyzer comprising: an excitation source positioned to excite particles within the blood sample; a plurality of detectors including (1) an axial light loss detector positioned to measure axial light loss from the excited blood sample, (2) an intermediate angle scatter detector positioned to measure intermediate angle scatters from the excited blood sample, (3) a polarized side scatter detector positioned to measure large angle polarized side scatters from the excited blood sample, (4) a depolarized side scatter detector positioned to measure large angle depolarized side scatters from the excited blood sample; and a processor configured to: (I) receive the measurements of (1) axial light loss, (2) intermediate angle scatters, (3) large angle polarized side scatters, (4) large angle depolarized side scatters, and (II) perform an MCV analysis of the blood sample, based on a plurality of data received from the detectors; and (b) a hematology reagent comprising: a non-phosphate organic buffer; a sphering surfactant; and an osmolality adjustment component, wherein the hematology reagent has sufficient optical clarity to facilitate optical analysis of the sample. In some embodiments, the subject systems can be used to conduct a complete blood sample analysis, such as, e.g., an MCV analysis, without the use of electrical impedance measurement equipment.

In some embodiments, the non-phosphate organic buffer is MES, MOPS, HEPES, or imidazole. In some embodiments, the concentration of the non-phosphate organic buffer in the reagent is at least about 0.5%. In some embodiments, the concentration of the non-phosphate organic buffer in the reagent ranges from about 0.5% up to about 20%. In some embodiments, the concentration of the non-phosphate organic buffer in the reagent is at least about 50 mM. In some embodiments, the concentration of the non-phosphate organic buffer in the reagent ranges from about 50 up to about 1,500 mM. In some embodiments, the sphering surfactant is maltoside. In some embodiments, the concentration of the sphering surfactant is at least about 0.0002%. In some embodiments, the concentration of the sphering surfactant ranges from about 0.0002% up to about 2.0%. In some embodiments, the concentration of the sphering surfactant is at least about 5 mg/L. In some embodiments, the concentration of the sphering surfactant ranges from about 5 up to about 1,000 mg/L. In some embodiments, the osmolality adjustment component is sodium chloride, potassium chloride or a mixture thereof. In some embodiments, the concentration of the osmolality adjustment component is at least about 0.25%. In some embodiments, the concentration of the osmolality adjustment component ranges from about 0.25% up to about 25%. In some embodiments, the reagent further comprises an antimicrobial agent. In some embodiments, the concentration of the antimicrobial agent is at least about 0.2%. In some embodiments, the concentration of the antimicrobial agent ranges from about 0.02% up to about 0.1%. In some embodiments, the pH of the reagent ranges from about 6.0 up to about 8.0 pH units. In some embodiments, the osmolality of a 1X concentration solution of the reagent ranges from about 250 up to about 350 mOsm. In some embodiments, the plurality of detectors includes one or more photomultiplier tubes and/or avalanche photo diodes (APDs). In some embodiments, the excitation source is a laser.

In some embodiments, the subject systems further include a subsystem for diluting the reagent. In some embodiments, the subsystem is configured to mix the diluted reagent with the blood sample. In some embodiments, the subsystem is configured to incubate the blood sample with the reagent for a period of time ranging from about 1 to about 30 seconds. In some embodiments, the subsystem is configured to incubate the blood sample with the diluted reagent at a temperature ranging from about 15° C. to about 50° C. In some embodiments, the subsystem is configured to incubate the blood sample with the diluted reagent at ambient temperature.

In some embodiments, the present disclosure provides methods for performing an optical mean corpuscular volume (MCV) analysis with an automated hematology analyzer, the method including: (a) diluting a sample of whole blood with a 1X concentration working solution of a hematology analysis reagent, wherein the hematology analysis reagent comprises: a non-phosphate organic buffer; a sphering surfactant; and an osmolality adjustment component, wherein the hematology reagent has sufficient optical clarity to facilitate optical analysis of the sample; (b) delivering the incubated sample from step (a) to a flow cell of the hematology analyzer; (c) exciting the incubated sample from step (b)

with an excitation source as the sample traverses the flow cell; (d) collecting a plurality of light scatter signals from the excited sample; and (e) analyzing the signals collected in step (d) to determine the MCV of the sample. In some embodiments, the subject methods involve conducting a complete blood sample analysis, such as, e.g., an MCV analysis, without the use of electrical impedance measurement equipment.

In some embodiments, the non-phosphate organic buffer is MES, MOPS, HEPES, or imidazole. In some embodiments, the concentration of the non-phosphate organic buffer in the reagent ranges from about 0.5% up to about 20%. In some embodiments, the concentration of the non-phosphate organic buffer in the reagent ranges from about 50 up to about 1,500 mM. In some embodiments, the sphering surfactant is maltoside. In some embodiments, the concentration of the sphering surfactant ranges from about 0.0002% up to about 2.0%. In some embodiments, the concentration of the sphering surfactant ranges from about 5 up to about 1,000 mg/L. In some embodiments, the osmolality adjustment component is sodium chloride, potassium chloride or a mixture thereof. In some embodiments, the concentration of the osmolality adjustment component ranges from about 0.25% up to about 25%. In some embodiments, the reagent further comprises an antimicrobial agent. In some embodiments, the concentration of the antimicrobial agent ranges from about 0.02% up to about 0.1%. In some embodiments, the pH of the reagent ranges from about 6.0 up to about 8.0 pH units. In some embodiments, the osmolality of a 1X concentration solution of the reagent ranges from about 250 up to about 350 mOsm.

In some embodiments, the present disclosure provides hematology reagents that include: a non-phosphate organic buffer; a sphering surfactant; and an osmolality adjustment component, wherein the hematology reagent has sufficient optical clarity to facilitate optical analysis of a blood sample.

In some embodiments, the non-phosphate organic buffer is MES, MOPS, HEPES, or imidazole. In some embodiments, the concentration of the non-phosphate organic buffer in the reagent is at least about 0.5%. In some embodiments, the concentration of the non-phosphate organic buffer in the reagent ranges from about 0.5% up to about 20%. In some embodiments, the concentration of the non-phosphate organic buffer in the reagent is at least about 50 mM. In some embodiments, the concentration of the non-phosphate organic buffer in the reagent ranges from about 50 up to about 1,500 mM. In some embodiments, the sphering surfactant is maltoside. In some embodiments, the concentration of the sphering surfactant is at least about 0.0002%. In some embodiments, the concentration of the sphering surfactant ranges from about 0.0002% up to about 2.0%. In some embodiments, the concentration of the sphering surfactant is at least about 5 mg/L. In some embodiments, the concentration of the sphering surfactant ranges from about 5 up to about 1,000 mg/L. In some embodiments, the osmolality adjustment component is sodium chloride, potassium chloride or a mixture thereof. In some embodiments, the concentration of the osmolality adjustment component is at least about 0.25%. In some embodiments, the concentration of the osmolality adjustment component ranges from about 0.25% up to about 25%. In some embodiments, the reagent further comprises an antimicrobial agent. In some embodiments, the concentration of the antimicrobial agent is at least about 0.02%. In some embodiments, the concentration of the antimicrobial agent ranges from about 0.02% up to about 0.1%. In some embodiments, the pH of the reagent ranges from about 6.0 up to about 8.0 pH units. In some embodiments, the osmolality of a 1X concentration solution of the reagent ranges from about 250 up to about 350 mOsm.

BRIEF DESCRIPTION OF THE FIGURES

The accompanying figures, which are incorporated herein, form part of the specification. Together with this written description, the figures further serve to explain the principles of, and to enable a person skilled in the relevant art(s), to make and use the reagents, systems and methods presented herein. In the figures, like reference numbers indicate identical or functionally similar elements.

DETAILED DESCRIPTION

Figure 1:
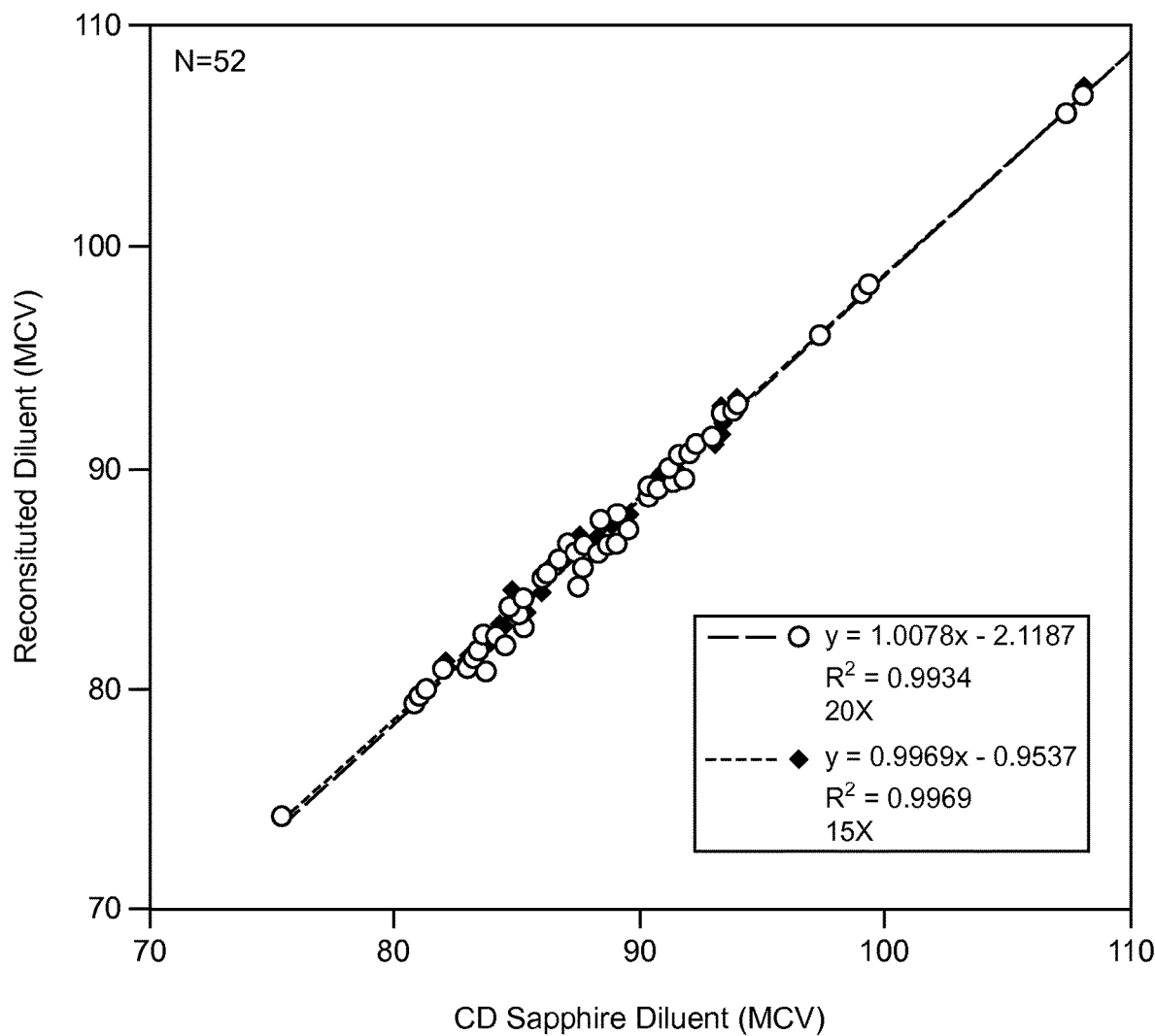
FIG. 1 shows a graph that correlates mean corpuscular volume (MCV) measurements taken using a 1X working solution of a hematology reagent described herein to MCV measurements taken using a standard CD Sapphire reagent.

Aspects of the invention include hematology analysis reagents, systems and methods that can be used to preserve blood cell morphology and uniformity as well as provide sample integrity and optical clarity to facilitate optical analysis of blood samples. In some embodiments, the subject reagents include a non-phosphate organic buffer and a sphering surfactant. The pH and osmolality of the reagents may be adjusted to desired ranges. In addition, the reagents can be simply reconstituted with de-ionized water prior to use.

Red blood cells (RBCs) are the most common type of blood cell, and generally have the shape of a bi-concave disk that is flattened and compressed in the center. Quantification of RBCs in a sample of blood is typically achieved using an impedance detector that measures changes in the electrical resistance of the sample as the sample passes through a small aperture. As each individual RBC passes through the aperture, a corresponding change in impedance is detected, and the information is used to count the number of RBCs in the sample. Since impedance measurements do not involve optical data collected from the cells, the shape of the RBCs is not critical to this analysis.

Hematological analysis systems and methods generally rely on both optical and electrical impedance measurements to analyze a blood sample and provide a differential analysis of the cells therein. For example, many hematology analyzers perform electrical impedance measurements on a sample to determine the number of RBCs and PLTs that are present in the sample, and also perform optical analyses to, e.g., quantify white blood cells (WBCs) and/or other components in the blood, and to provide additional optical analysis of RBCs and PLTs. Accordingly, most hematology analyzers must include both optical data collection components, as well as electrical impedance measurement components to provide a complete analysis of a blood sample.

The hematology analysis reagents, systems and methods according to the present disclosure provide for optical analysis of blood samples and obviate the need for hematology analyzers to include electrical impedance measurement components. As such, the subject hematology analysis reagents, systems and methods can be used to carry out a complete analysis of a blood sample using only optical data collection components, e.g., without using electrical impedance measurements.

Hematology Analysis Reagents

The hematology analysis reagents provided herein are generally designed to facilitate complete analysis of a blood sample without the use of electrical impedance components. For example, the hematology analysis reagents provided herein provide a number of features that facilitate optical analysis of RBCs, and therefore obviate the need for electrical impedance measurements. The subject hematology reagents provide optical clarity that is necessary for optical analysis of blood samples, and also provide for sphering of RBCs so that they can be analyzed using optical techniques. The subject hematology reagents can also be highly concentrated while still maintaining their functional characteristics, which facilitates improved manufacturability, storage and handling of the reagents.

Non-Phosphate Organic Buffer

The subject hematology reagents generally include one or more non-phosphate organic buffers. The use of these buffers provides enhanced solubility of other components of the reagent, such as, e.g., sodium chloride as a primary osmolyte. Phosphate-based buffer components, such as phosphate buffered saline (PBS), generally cause solubility issues at high concentrations. Non-phosphate organic buffers, in contrast, are generally inert to other reagent components, such as salts, and therefore allow more concentrated reagents to be formulated while still maintaining functional properties, such as, e.g., optical clarity. Non-phosphate organic buffers in accordance with some embodiments of the invention generally have an effective buffering capacity between pH 6.0 and 8.0. Examples of suitable non-phosphate organic buffers include, but are not limited to, 2-(N-morpholine) ethane sulfonic acid (MES) buffer, 3-(N-morpholine) propane sulfonic acid (MOPS) buffer, imidazole, and N-(2-hydroxyethyl) piperazine-N'-(2-ethane sulfonic acid) (HEPES) buffer.

In some embodiments, the concentration of the non-phosphate organic buffer in the hematology reagent ranges from about 50, up to about 75, up to about 100, up to about 125, up to about 150, up to about 175, up to about 200, up to about 225, or up to about 250, up to about 275, up to about 300, up to about 325, up to about 350, up to about 375, up to about 400, up to about 425, up to about 450, up to about 475, up to about 500, up to about 525, up to about 550, up to about 575, up to about 600, up to about 625, up to about 650, up to about 675, up to about 700, up to about 725, up to about 750, up to about 775, up to about 800, up to about 825, up to about 850, up to about 875, up to about 900, up to about 925, up to about 950, up to about 1000, up to about 1050, up to about 1100, up to about 1150, up to about 1200, up to about 1250, up to about 1300, up to about 1350, up to about 1400, up to about 1450, up to about 1500 mM or more.

In some embodiments, the concentration of the non-phosphate organic buffer in the hematology reagent ranges from about 0.5%, up to about 1.0%, up to about 1.5%, up to about 2.0%, up to about 2.5%, up to about 3.0%, up to about 3.5%, up to about 4.0%, up to about 4.5%, up to about 5.0%, up to about 5.5%, or up to about 6.0% up to about 6.5%, up to about 7.0%, up to about 7.5%, up to about 8.0%, up to about 8.5%, up to about 9.0%, up to about 9.5%, up to about 10.0%, up to about 10.5%, up to about 11.0%, up to about 11.5%, up to about 12.0%, up to about 12.5%, up to about 13.0%, up to about 13.5%, up to about 14.0%, up to about 14.5%, up to about 15.0%, up to about 15.5%, up to about 16.0%, up to about 16.5%, up to about 17.0%, up to about 17.5%, up to about 18.0%, up to about 18.5%, up to about 19.0%, up to about 19.5%, up to about 20.0% or more.

Sphering Surfactant

The subject hematology reagents generally include one or more sphering surfactants that sphere RBCs in the blood sample to facilitate their optical analysis. The use of such surfactants sustains a sphered cell morphology in diluted blood samples and facilitates optical analyses, e.g., optical mean corpuscular volume (MCV) analysis. Examples of suitable sphering surfactants include, but are not limited to, N-dodecyl-B-D-maltoside (maltoside).

In some embodiments, the concentration of the sphering surfactant in the hematology reagent ranges from about 0.0002%, up to about 0.0005%, up to about 0.001%, up to about 0.005%, up to about 0.01%, up to about 0.05%, up to about 0.1%, up to about 0.5%, up to about 1.0%, up to about 1.25%, up to about 1.5%, up to about 1.75%, or up to about 2.0% or more. In some embodiments, the concentration of the sphering surfactant ranges from about 5, up to about 25, up to about 50, up to about 75, up to about 100, up to about 200, up to about 300, up to about 400, up to about 500, up to about 600, up to about 700, up to about 800, up to about 900, up to about 1,000 mg/L or more.

Additional Components

Hematology reagents in accordance with embodiments of the invention may contain additional components, such as, e.g., chelating reagents, salts or osmolytes. For example, in some embodiments, a hematology reagent may contain a chelating reagent to, e.g., prevent platelet clumping and/or aggregation. An example of a suitable chelating reagent is ethylenediaminetetraacetate (EDTA) or EDTA di-sodium salt.

In some embodiments, a chelating reagent may be present in a hematology reagent at a concentration ranging from about 0.1%, up to about 0.2%, up to about 0.3%, up to about 0.4%, up to about 0.5% or more.

In some embodiments, a hematology reagent may contain an osmolality adjusting component, such as, e.g., a salt. The inclusion of one or more salts in the hematology reagent serves to adjust the osmolality of the reagent for optimum performance. Suitable examples of salts include, but are not limited to, sodium chloride and potassium chloride.

In some embodiments, an osmolality adjusting component (e.g., a salt) may be present in a hematology reagent at a concentration ranging from about 0.25%, up to about 0.5%, up to about 0.75%, up to about 1%, up to about 5%, up to about 10%, up to about 15%, up to about 20%, or up to about 25% or more.

Hematology reagents in accordance with some embodiments of the invention may have a pH value that is adjusted for optimum performance of the reagent. For example, in some embodiments, a hematology reagent may have a pH value ranging from about 6.0, up to about 6.25, up to about 6.5, up to about 6.75, up to about 7.0, up to about 7.25, up to about 7.5, up to about 7.75, up to about 8.0 pH units. In some embodiments, the pH of a hematology reagent may be adjusted using standard pH adjustment reagents, e.g., concentrated acids or bases.

Hematology reagents in accordance with some embodiments of the invention may have an osmolality that is adjusted for optimum performance of the reagent. Prior to its dilution to a working concentration, hematology reagents in accordance with some embodiments may have an osmolality that is hypertonic. After dilution of the hematology reagent to a 1X working concentration, in some embodiments the hematology reagent may have an osmolality ranging from about 250, up to about 260, up to about 270, up to about 280, up to about 290, up to about 300, up to about 310, up to about 320, up to about 330, up to about 340, up to about 350 mOsm or more.

In some embodiments, a hematology reagent may include at least one preservative and/or at least one antimicrobial agent to prevent microbial growth in the reagent. Suitable examples of antimicrobial agents include, but are not limited to, TRIADINE® (Sodium, 2-pyridinethiol-1-oxide, Hexahydro-1,3,5-tris (2-hydroxyethyl)-s-triazine, and inert ingredients) or equivalents thereof. In some embodiments, the concentration of the antimicrobial reagent ranges from about 0.02%, up to about 0.04%, up to about 0.06%, up to about 0.08%, up to about 0.1% or more.

In some embodiments, the concentrations of the various components in the hematology reagent are balanced and optimized to facilitate the incorporation of only minimal quantities of certain components while still maintaining the functional properties of the reagent. For example, in some embodiments, the concentration of salts and non-phosphate organic buffers included in the reagent facilitate the use of lower quantities of the sphering surfactant. This balancing of the components helps to reduce the overall cost of the reagent and improve the manufacturability of the reagent.

In some embodiments, the concentrations of the various components in the hematology reagent are balanced to facilitate handling of the reagent. For example, in some embodiments, the concentrations of each component are carefully controlled so that the reagent maintains its functional properties and maintains solubility of the components, even when the reagent is subjected to one or more freeze/thaw cycles.

Example Formulations:

Various example formulations of the subject hematology reagents are provided below. The formulations provided below merely serve as examples, and are in no way limiting. Any of a variety of combinations of the components described herein can be utilized in hematology reagents in accordance with embodiments of the invention. Triadine 10 is TRIADINE® 10 (Sodium, 2-pyridinethiol-1-oxide, 6.56%, Hexahydro-1,3,5-tris (2-hydroxyethyl)-s-triazine 65.95%, and inert ingredients 27.54%).

Example Formulation 1:

| Component | Concentration |
|---|---|
| EDTA di-sodium salt | 0.30% |
| Potassium Chloride | 0.45% |
| Sodium Chloride | 15.70% |
| Triadine 10 | 0.06% |
| N-Dodecyl-B-D, Maltoside | 0.02% |
| Imidazole | 0.60% |

The above formulation can be diluted by 15X to form a 1X working reagent.

Example Formulation 2:

| Component | Concentration |
|---|---|
| EDTA di-sodium salt | 0.30% |
| Potassium Chloride | 0.45% |
| Sodium Chloride | 15.70% |
| Triadine 10 | 0.06% |
| N-Dodecyl-B-D, Maltoside | 0.02% |
| MES | 2.30% |

The above formulation can be diluted by 15X to form a 1X working reagent.

Example Formulation 3:

| Component | Concentration |
|---|---|
| EDTA di-sodium salt | 0.30% |
| Potassium Chloride | 0.45% |
| Sodium Chloride | 15.70% |
| Triadine 10 | 0.06% |
| N-Dodecyl-B-D, Maltoside | 0.02% |
| HEPES | 3.50% |

The above formulation can be diluted by 15X to form a 1X working reagent.

Example Formulation 4:

| Component | Concentration |
|---|---|
| EDTA di-sodium salt | 0.40% |
| Potassium Chloride | 0.30% |
| Sodium Chloride | 21.24% |
| Triadine 10 | 0.06% |
| N-Dodecyl-B-D, Maltoside | 0.02% |
| Imidazole | 0.80% |

The above formulation can be diluted by 20X to form a 1X working reagent.

Example Formulation 5 (A-I):

A series of reagent formulations (A-I) are provided below, wherein the concentration of sodium chloride was varied as indicated:

| Component | A | B | C | D | E | F | G | H | I |
|---|---|---|---|---|---|---|---|---|---|
| EDTA di-sodium salt | 0.40% | 0.40% | 0.40% | 0.40% | 0.40% | 0.40% | 0.40% | 0.40% | 0.40% |
| Potassium Chloride | 0.30% | 0.30% | 0.30% | 0.30% | 0.30% | 0.30% | 0.30% | 0.30% | 0.30% |
| Sodium | 20.39% | 20.60% | 20.82% | 21.03% | 21.24% | 21.45% | 21.66% | 21.88% | 22.09% |

-continued

| Component | A | B | C | D | E | F | G | H | I |
|---|---|---|---|---|---|---|---|---|---|
| Chloride | | | | | | | | | |
| Triadine 10 | 0.06% | 0.06% | 0.06% | 0.06% | 0.06% | 0.06% | 0.06% | 0.06% | 0.06% |
| N-Dodecyl-B-D, Maltoside | 0.02% | 0.02% | 0.02% | 0.02% | 0.02% | 0.02% | 0.02% | 0.02% | 0.02% |
| Imidazole | 0.80% | 0.80% | 0.80% | 0.80% | 0.80% | 0.80% | 0.80% | 0.80% | 0.80% |
| Osmolality (mOsmo/kg) of 1X working reagent | 313 | 317 | 319 | 322 | 322 | 325 | 329 | 331 | 335 |

Example Formulation 6 (A-G):

A series of reagent formulations (A-G) are provided below, wherein the pH value of the reagent varied as indicated. Concentrated HCl was added to each formulation in a sufficient quantity to adjust the pH to the values indicated below.

| Component | A | B | C | D | E | F | G |
|---|---|---|---|---|---|---|---|
| EDTA di-sodium salt | 0.40% | 0.40% | 0.40% | 0.40% | 0.40% | 0.40% | 0.40% |
| Potassium Chloride | 0.30% | 0.30% | 0.30% | 0.30% | 0.30% | 0.30% | 0.30% |
| Sodium Chloride | 21.24% | 21.24% | 21.24% | 21.24% | 21.24% | 21.24% | 21.24% |
| Triadine 10 | 0.06% | 0.06% | 0.06% | 0.06% | 0.06% | 0.06% | 0.06% |
| N-Dodecyl-B-D, Maltoside | 0.02% | 0.02% | 0.02% | 0.02% | 0.02% | 0.02% | 0.02% |
| Imidazole | 0.80% | 0.80% | 0.80% | 0.80% | 0.80% | 0.80% | 0.80% |
| pH | 6.95 | 7.20 | 7.35 | 7.45 | 7.55 | 7.70 | 7.95 |

Example Formulation 7 (A-G):

A series of reagent formulations (A-G) are provided below, wherein the concentration of maltoside in the reagent varied as indicated:

| Component | A | B | C | D | E | F | G |
|---|---|---|---|---|---|---|---|
| EDTA di-sodium salt | 0.40% | 0.40% | 0.40% | 0.40% | 0.40% | 0.40% | 0.40% |
| Potassium Chloride | 0.30% | 0.30% | 0.30% | 0.30% | 0.30% | 0.30% | .30% |
| Sodium Chloride | 21.24% | 21.24% | 21.24% | 21.24% | 21.24% | 21.24% | 21.24% |
| Triadine 10 | 0.06% | 0.06% | 0.06% | 0.06% | 0.06% | 0.06% | 0.06% |
| N-Dodecyl-B-D, Maltoside | −5% | −2.5% | −1% | 0.0% | +1% | +2.5% | +5% |
| Imidazole | 0.80% | 0.80% | 0.80% | 0.80% | 0.80% | 0.80% | 0.80% |

Systems and Methods

The hematology reagents disclosed herein generally find use in the optical analysis of blood samples using hematology analysis systems and related methods. In certain embodiments, the subject hematology reagents find use in hematology analysis systems and methods that are designed to optically measure RBCs in a sample of blood. For example, in some embodiments the subject systems and methods may be used to perform a complete blood sample analysis without the use of electrical impedance measurements, e.g., using only optical measurements.

In some embodiments, the subject hematology reagents are diluted with a suitable reagent, e.g., de-ionized water, prior to their use in analyzing a blood sample. For example, in some embodiments, a subject hematology reagent may be diluted by a factor of about 2X, up to about 5X, up to about 10X, up to about 15X, up to about 20X, or up to about 25X to form a working solution of the reagent that has a concentration of 1X.

In some embodiments, a subject hematology reagent may be diluted to an appropriate concentration using simple mixing techniques, for example, wherein the reagent is mixed with de-ionized water in a container of a suitable size and mechanically mixed, stirred, etc. In some embodiments, mixing of the hematology reagent with de-ionized water can be accomplished using, e.g., an electronic mixing device.

In some embodiments, a working solution of the reagent may be created prior to its use in a hematology analyzer. For example, in some embodiments a working solution having a concentration of 1X of the hematology reagent is formed as described above, and the 1X working solution is then introduced into or fluidly coupled to a hematology analyzer for use in analyzing a blood sample. In some embodiments, a concentrated form of the subject hematology reagents may be introduced into or fluidly coupled to a hematology analyzer, and the analyzer may perform a dilution of the hematology reagent prior to or concurrent with the analysis of a blood sample.

In certain embodiments, a 1X concentration working solution of a subject hematology reagent is mixed with a blood sample, and the blood sample is analyzed on an automated hematology analyzer that generates a plurality of optical data from the sample be directing a light source towards the sample as it is passed through a flow cell. In some embodiments, the hematology analyzer may include a processor containing instructions that, when executed by the processor, cause the hematology analyzer to carry out a series of steps that involve moving a sample through the flow cell of the analyzer, directing light towards the flow cell, gathering a plurality of optical data from the sample, and analyzing the optical data to determine, e.g., an MCV measurement from the sample based on the optical data.

Aspects of the invention also include methods of analyzing a blood sample to determine the MCV of the sample using optical techniques. For example, methods in accordance with embodiments of the invention involve: (a) contacting a blood sample with a 1X working solution of a reagent that comprises at least one non-phosphate organic buffer, at least one sphering surfactant, and one or more osmolality adjustment components and incubating the blood sample with the reagent for a period of time ranging from about 1 to about 30 seconds at a temperature ranging from about 15° C. up to about 50° C., such as, e.g., ambient temperature; (b) delivering the sample from step (a) to a flow cell of a hematology analyzer; (c) exciting the sample from step (b) with an excitation source as the sample traverses the flow cell; (d) collecting a plurality of light scatter signals from the excited sample; and (e) analyzing the signals collected in step (d) to the determine the MCV of the sample.

EXAMPLES

Example 1: MCV Measurement Comparison Using Different Reagents

Figure 2:
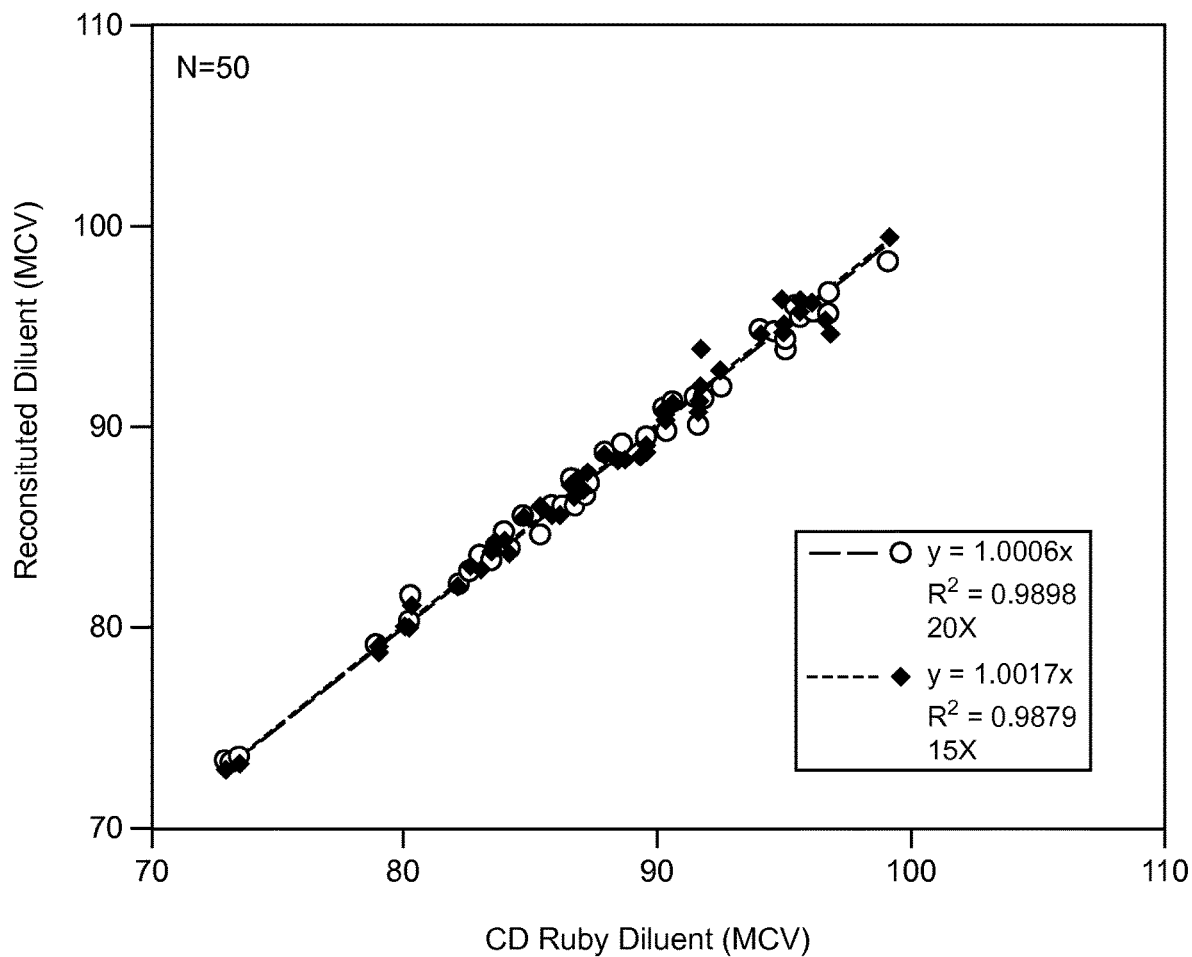
FIG. 2 shows a graph that correlates MCV measurements taken using a 1X working solution of a hematology reagent described herein to MCV measurements taken using a standard CD Ruby reagent.

MCV measurements were taken on a normal blood sample using a subject hematology reagent that was diluted from 15X or 20X to form a solution of 1X concentration. The MCV measurements were compared with MCV measurements that were taken on the same normal blood sample using a CD Sapphire or CD Ruby reagent. The results are shown in FIG. 1 and FIG. 2. The results show that the subject hematology reagents perform equally well using either impedance or optical detection systems.

Example 2:

Impact of Osmolality Variation on Optical MCV Measurements

Figure 3:
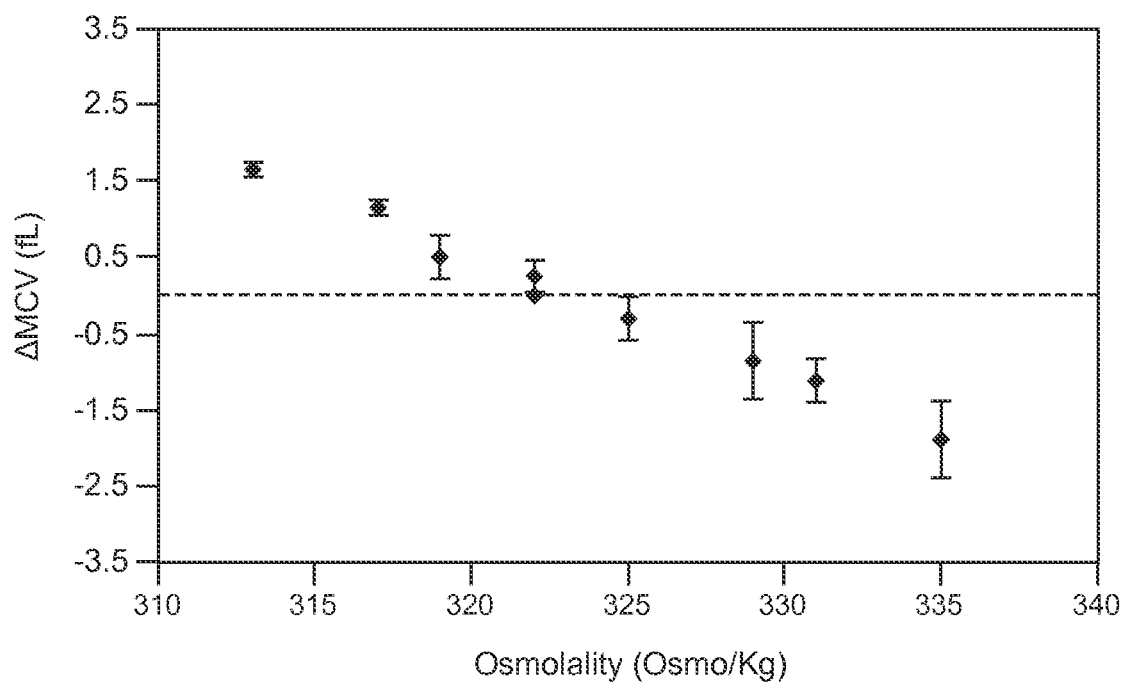
FIG. 3 is a graph that shows the impact of changes in the osmolality of a hematology reagent on optical MCV measurements.

A series of reagents was formulated having different sodium chloride concentrations to adjust the final osmolality of the working reagent when used in a hematology analyzer to measure MCV. The concentrations of the components in the reagents are shown in example formulations 5A-I. The reagents were then used to measure the MCV of a normal blood sample on a hematology analyzer. The results are shown in FIG. 3, and indicate that the formulations function as expected over the tested osmolality range.

Example 3: Impact of pH Variation on Optical MCV Measurements

Figure 4:
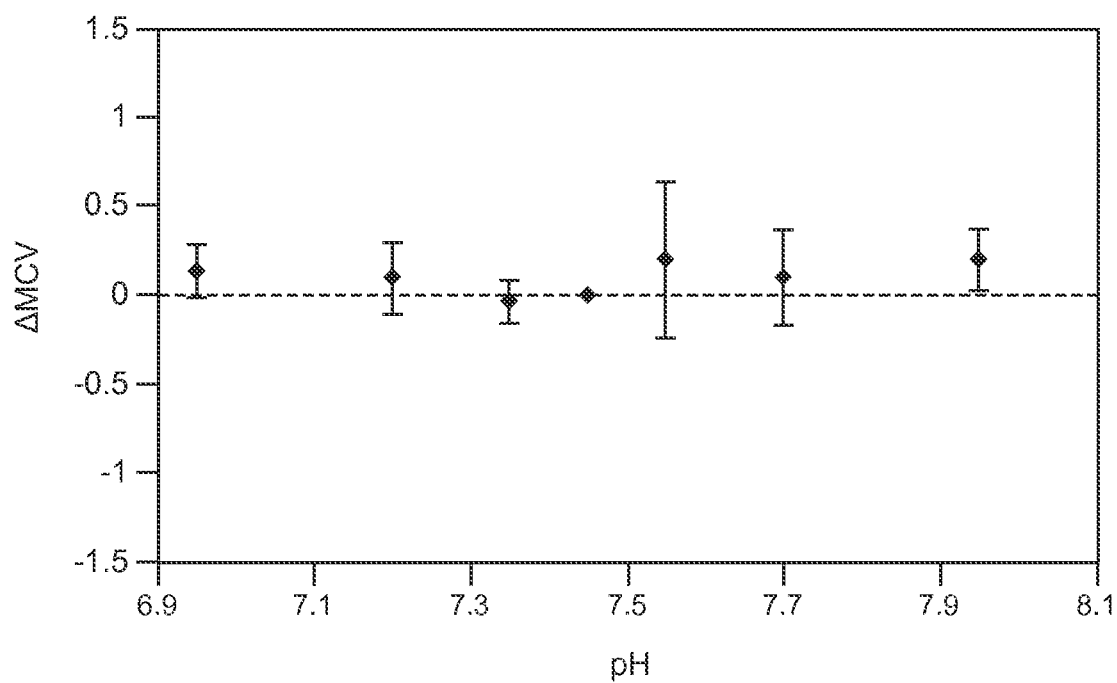
FIG. 4 is a graph that shows the impact of changes in the pH of a hematology reagent on optical MCV measurements.

A series of reagents was formulated having different pH values. The concentrations of the components in the reagents are shown in example formulations 6A-G. The reagents were then used to measure the MCV of a normal blood sample on a hematology analyzer. The results are shown in FIG. 4, and indicate that the formulations function as expected over the tested pH range.

Example 4: Impact of Maltoside Variation on Optical MCV Measurements

Figure 5:
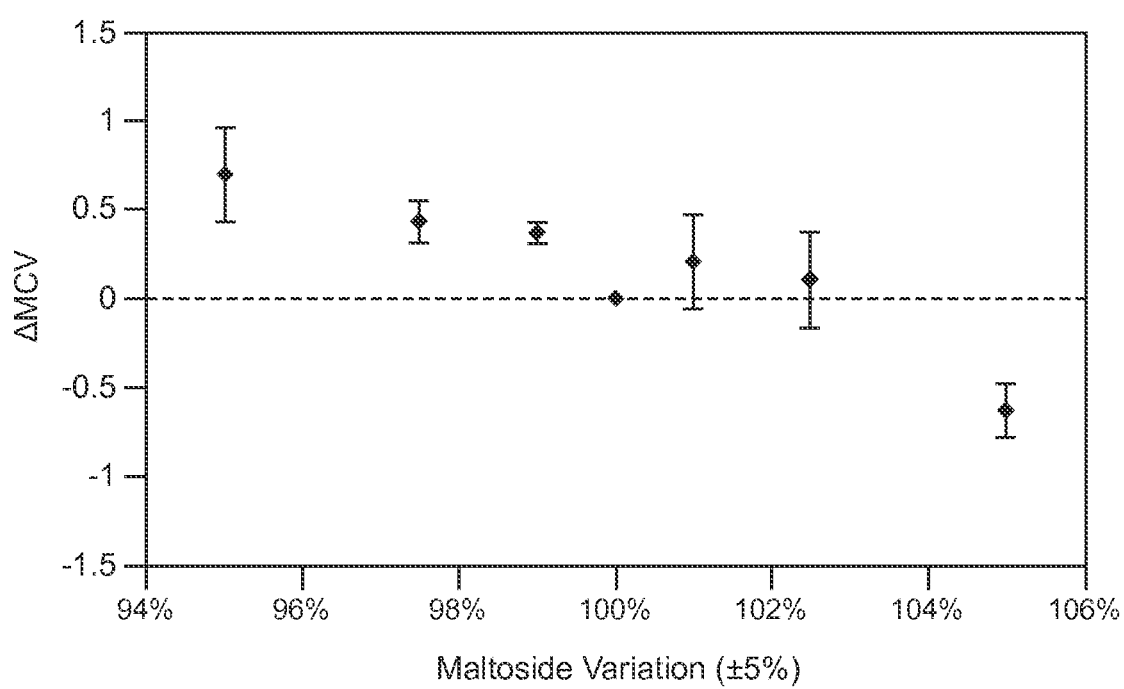
FIG. 5 is a graph that shows the impact of changes in the maltoside concentration of a hematology reagent on optical MCV measurements.

A series of reagents was formulated having different maltoside concentrations. The concentrations of the components in the reagents are shown in example formulations 7A-G. The reagents were then used to measure the MCV of a normal blood sample on a hematology analyzer. The results are shown in FIG. 5, and indicate that the formulations function as expected over the tested maltoside concentration range.

The foregoing description of the invention has been presented for purposes of illustration and description. It is not intended to be exhaustive or to limit the invention to the precise form disclosed. Other modifications and variations may be possible in light of the above teachings. The embodiments were chosen and described in order to best explain the principles of the invention and its practical application, and to thereby enable others skilled in the art to best utilize the invention in various embodiments and various modifications as are suited to the particular use contemplated. It is intended that the appended claims be construed to include other alternative embodiments of the invention; including equivalent structures, components, methods, and means.

The above Detailed Description refers to the accompanying drawings that illustrate one or more exemplary embodiments. Other embodiments are possible. Modifications may be made to the embodiment described without departing from the spirit and scope of the present invention. Therefore, the Detailed Description is not meant to be limiting. Further, the Summary and Abstract sections may set forth one or more, but not all exemplary embodiments of the present invention as contemplated by the inventor(s), and thus, are not intended to limit the present invention and the appended claims in any way.

What is claimed is:

1. A method of performing an optical mean corpuscular volume (MCV) analysis of red blood cells (RBCs) with an automated hematology analyzer, the method consisting of:
    (a) diluting a sample of whole blood with a hematology analysis reagent, wherein the hematology analysis reagent comprises:
        a non-phosphate organic buffer;
        a sphering surfactant; and
        an osmolality adjustment component,
    wherein the hematology analysis reagent does not include a phosphate buffered reagent and wherein the hematology analysis reagent has sufficient optical clarity to facilitate optical analysis of the sample;
    (b) incubating the diluted sample from step (a) for a period of time ranging from 1 second to 30 seconds;
    (c) providing instructions that, when executed by a processor, cause the hematology analyzer to perform steps (d) through (g):
    (d) deliver the incubated sample from step (b) to a flow cell of the hematology analyzer;
    (e) direct light from an excitation source towards the flow cell for exciting the incubated sample from step (d) as the sample traverses the flow cell;
    (f) collect a plurality of light scatter signals from the excited sample; and
    (g) analyze the plurality of light scatter signals collected in step (f) to determine the MCV of red blood cells in the sample.

2. The method according to claim 1, wherein the non-phosphate organic buffer is 2-(N-morpholine) ethane sulfonic acid (MES), 3-(N-morpholine) propane sulfonic acid (MOPS), N-(2-hydroxyethyl) piperazine-N'-(2-ethane sulfonic acid) (HEPES), or imidazole.

3. The method according to claim 1, wherein the concentration of the non-phosphate organic buffer in the reagent ranges from 0.5% up to 20%.

4. The method according to claim 1, wherein the concentration of the non-phosphate organic buffer in the reagent ranges from 50 up to 1,500 mM.

5. The method according to claim 1, wherein the sphering surfactant is maltoside.

6. The method according to claim 1, wherein the concentration of the sphering surfactant ranges from 0.0002% up to 2.0%.

7. The method according to claim 1, wherein the concentration of the sphering surfactant ranges from 5 up to 1,000 mg/L.

8. The method according to claim 1, wherein the osmolality adjustment component is sodium chloride, potassium chloride or a mixture thereof.

9. The method according to claim 1, wherein the concentration of the osmolality adjustment component ranges from 0.25% up to 25%.

10. The method according to claim 1, wherein the reagent further comprises an antimicrobial agent.

11. The method according to claim 10, wherein the concentration of the antimicrobial agent ranges from 0.02% up to 0.1%.

12. The method according to claim 1, wherein the pH of the reagent ranges from 6.0 up to 8.0 pH units.

13. The method according to claim 1, wherein the osmolality of the hematology analysis reagent ranges from 50 up to 350 mOsm.

14. The method according to claim 1, wherein the hematology analysis reagent is made by diluting a 15X concentrated solution to a 1X working solution.

15. The method according to claim 2, wherein the concentration of the non-phosphate organic buffer in the reagent ranges from 50 mM-1500 mM, the concentration of the sphering surfactant ranges from 0.0002%-2.0%, the concentration of the osmolality adjustment component ranges from 0.25%-25%, the concentration of the antimicrobial agent ranges from 0.02%-0.1%, and the osmolality of the hematology analysis reagent ranges from 250 mOsm-350 mOsm.

16. The method according to claim 15, wherein the hematology analysis reagent is made by diluting a 15X concentrated solution to a 1X working solution.

17. The method according to claim 15, wherein the hematology analysis reagent is made by diluting a 20X concentrated solution to a 1X working solution.

18. The method according to claim 15, wherein the sphering surfactant is dodecyl-B-D-maltoside.

19. The method according to claim 15, wherein the osmolality adjustment component is a mixture of sodium chloride and potassium chloride.

20. The method according to claim 1, wherein analyzing the light signals to determine the MCV of the sample is conducted without the use of electrical impedance measurement equipment.

21. The method according to claim 11, wherein the concentration of the antimicrobial agent is 0.06%.

22. The method according to claim 1, wherein the plurality of light scatter signals that are analyzed to determine MCV are only axial light loss signals and intermediate angle scatter signals.

* * * * *